US008274058B1

(12) United States Patent
Wanke et al.

(10) Patent No.: US 8,274,058 B1
(45) Date of Patent: Sep. 25, 2012

(54) INTEGRATED HETERODYNE TERAHERTZ TRANSCEIVER

(75) Inventors: Michael C. Wanke, Albuquerque, NM (US); Mark Lee, Albuquerque, NM (US); Christopher D. Nordquist, Albuquerque, NM (US); Michael J. Cich, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 742 days.

(21) Appl. No.: 12/488,612

(22) Filed: Jun. 22, 2009

Related U.S. Application Data

(63) Continuation-in-part of application No. 11/698,010, filed on Jan. 25, 2007, now Pat. No. 7,550,734.

(60) Provisional application No. 60/761,871, filed on Jan. 25, 2006.

(51) Int. Cl.
*G01T 1/24* (2006.01)
(52) U.S. Cl. .................................. 250/370.12
(58) Field of Classification Search ............. 250/370.12, 250/341.8; 257/E31.066; 702/75; 455/189.1
See application file for complete search history.

(56) References Cited

U.S. PATENT DOCUMENTS 5,631,489 A * 5/1997 Roser ............................ 257/449

OTHER PUBLICATIONS

H.-W. Hubers et al, "Terahertz quantum cascade laser as local oscillator in a heterodyne receiver", Optics Express, vol. 13, No. 15, Jul. 25, 2005, pp. 5890-5896.

Qing Hu et al, "Resonant-phonon-assisted THz quantum-cascade lasers with metal-metal waveguides", Semiconductor Science and Technology, 2005, vol. 20, pp. S228-S236.
J.R. Gao et al, "Terahertz heterodyne receiver based on a quantum cascade laser and a superconducting bolometer," Applied Physics Letters, 2005, vol. 86 pp. 244104-1 through 244104-3.
Stephen Kohen, et al "Electromagnetic modeling of terahertz quantum cascade laser waveguides and resonators," Journal of Applied Physics, vol. 97, 2005, pp. 053106-1 through 053106-9.
R. Sachs et al, "Mode calculations for a terahertz quantum cascade laser," Optics Express, vol. 12, No. 10, May 17, 2004, pp. 2062-2069.
Olivier Demichel et al, "Surface Plasmon photonic structures in terahertz quantum cascade lasers," Optics Express, vol. 14, No. 12, Jun. 12, 2006, pp. 5335-5345.
Rudeger Kohler et al, "Terahertz semiconductor-heterostructure laser," Nature, vol. 417, May 9, 2002, pp. 156-159.
A. Baryshev et al, "Phase locking and spectral linewidth of a two-mode terahertz quantum cascade laser", Applied Physics Letters, vol. 89, (2006), pp. 031115-1 thru 031115-3.
S. Barbien et al, "THz quantum cascade lasers operating up to 70 K in continuous wave", Applied Physics Letters, vol. 85, No. 10, (2004) pp. 1674-1676.

* cited by examiner

*Primary Examiner* — David Porta
*Assistant Examiner* — Faye Boosalis
(74) *Attorney, Agent, or Firm* — Kevin W. Bieg

(57) ABSTRACT

A heterodyne terahertz transceiver comprises a quantum cascade laser that is integrated on-chip with a Schottky diode mixer. A terahertz signal can be received by an antenna connected to the mixer, an end facet or sidewall of the laser, or through a separate active section that can amplify the incident signal. The quantum cascade laser couples terahertz local oscillator power to the Schottky diode to mix with the received terahertz signal to provide an intermediate frequency output signal. The fully integrated transceiver optimizes power efficiency, sensitivity, compactness, and reliability. The transceiver can be used in compact, fieldable systems covering a wide variety of deployable applications not possible with existing technology.

14 Claims, 14 Drawing Sheets

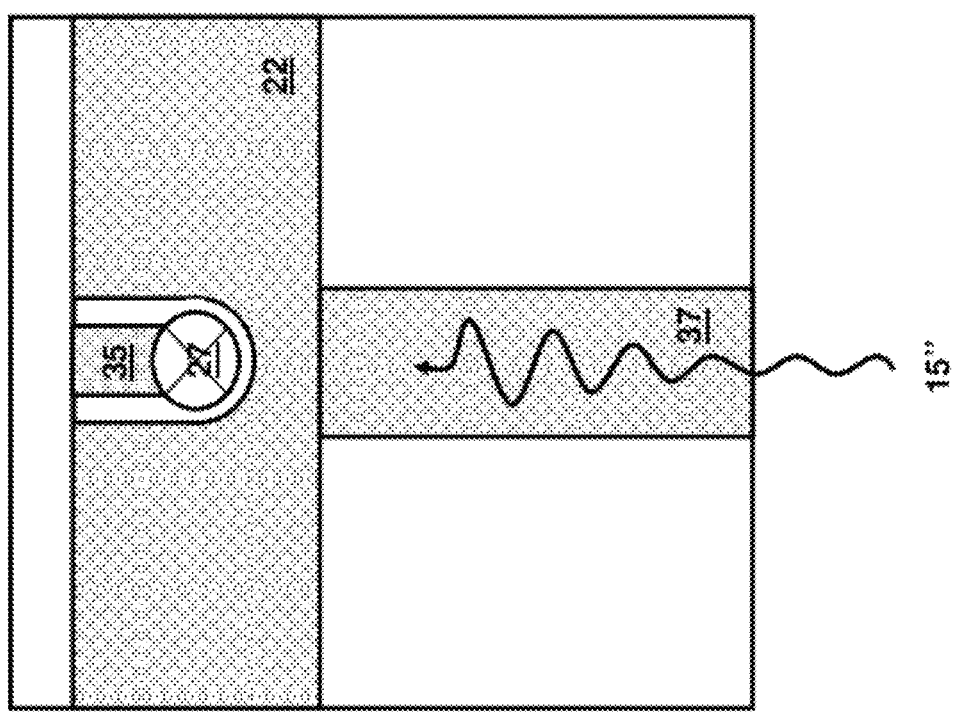

INTEGRATED HETERODYNE TERAHERTZ TRANSCEIVER

CROSS-REFERENCE TO RELATED APPLICATION

This application is a continuation-in-part of application Ser. No. 11/698,010, filed Jan. 25, 2007 now U.S. Pat. No. 7,550,734, which claimed the benefit of U.S. Provisional Application No. 60/761,871, filed Jan. 25, 2006, both of which are incorporated herein by reference.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to terahertz radiation technology and, in particular, to a microelectronics-based integrated heterodyne terahertz transceiver.

BACKGROUND OF THE INVENTION

Terahertz (THz) technologies utilize electromagnetic radiation generally in the frequency range between 100 GHz and 10 THz (i.e., wavelengths of 3 mm to 30 µm, energies of 0.4 to 40 meV, or equivalent blackbody radiation temperatures of 5 K to 500 K). Terahertz technologies have many potential applications in diverse fields, including space and atmospheric sciences, molecular spectroscopy, remote sensing, biology, medical imaging, and communications.

However, beyond basic science, these applications in the terahertz region are relatively undeveloped. In particular, the generation and detection of electromagnetic fields at terahertz frequencies has been difficult. To date, active terahertz generators have only demonstrated relatively low power capability. Recently, terahertz sources based on quantum cascade lasers (QCLs) have produced relatively high power in a compact size. QCLs are the first semiconductor sources of terahertz radiation capable of average powers in a pulsed mode in excess of 250 mW at cryogenic temperatures. QCLs are unipolar semiconductor devices comprising complex layered heterostructures of two or more semiconductor alloys forming an active waveguide core, typically mounted on a metallic heat-sink. The complex QCL structure can be grown by molecular beam epitaxy (MBE). MBE enables accurate control of the sub-nanometer semiconductor layers with high reproducibility over hundreds of periodic layers.

Quantum cascade lasers rely on the emission from transitions between subbands in a quantum well. Light is produced in an active region by intersubband transitions of a single charge carrier (i.e., an electron) between two quantized levels in the conduction band. In a QCL biased at an operating voltage, a photon is emitted by an intrawell transition between an upper level and a lower level in an active region. To achieve population inversion for lasing, electrons must be injected rapidly into the upper level and then rapidly extracted from the lower level and tunnel into the upper level of the downstream active region. To maximize the gain, tens to hundreds of these active regions can be cascaded together, enabling electrons that are recycled from one active region to the next to emit more than one photon per pass through the device, enabling high emission power. Because the energy difference between the two quantized levels is determined by the specific structure design (i.e., the quantum well and barrier widths), the laser can be band-structure engineered to emit at any wavelength within a broad spectral range. To minimize device loses and confine the terahertz radiation to the gain material, the active region can be inserted into a waveguide. Laser action requires that the gain be adequate to overcome device losses, primarily due to free-carrier losses in the waveguide and mirror losses. Many variations on this basic scheme have evolved.

However, the weak radiation output from passive and traditional active terahertz sources, the low photon energies of terahertz radiation, and high atmospheric attenuation due to molecular absorption (e.g., water vapor) frequently results in a weak received terahertz signal that may be difficult to distinguish from noise. Therefore, terahertz detection can also be difficult. Current terahertz detectors include both direct and heterodyne detectors.

Direct detectors generally directly convert the received power to a voltage or current that is proportional to the incoming power. Examples of direct detectors include rectifiers, bolometers, and pyroelectrics. A common direct detector uses antenna coupling to a small area Schottky diode that responds directly to the terahertz electric field. Detection depends on the nonlinear rectification properties of a metal-semiconductor junction. Advantages of the Schottky diode include a useful sensitivity over a large wavelength range, large instantaneous bandwidth, excellent performance at room temperature, and ease of fabrication.

For shorter wavelengths (i.e., frequencies above 1 THz), direct detectors generally have good responsivity and are sensitive to a broad band of frequencies. However, direct detectors generally provide no frequency discrimination, unless they are coupled with an external resonator or interferometer. Furthermore, they are sensitive to incoherent background noise and interference. Finally, direct directors are typically very slow, with 1 to 10 ms response times required to obtain an adequate signal-to-noise. Therefore, direct detectors have been used mainly for wideband applications, such as thermal imaging.

Heterodyned detection is desirable for some terahertz applications. Especially at low pressures such as a space environment, terahertz signatures of many molecules are very unique, enabling identification even with only a few spectral lines over a narrow spectral region. However, because the emission lines can be quite narrow and may be closely spaced, high resolution spectroscopy is desirable to take full advantage of terahertz discrimination capabilities. High-resolution heterodyne detection covering the frequency intervals of expected signatures is highly desirable for these applications. Further, particularly for weak signals, heterodyning can be used to coherently downconvert the terahertz signal to increase signal-to-noise by reducing bandwidth. The downconverted signal can then be post-amplified and processed using conventional microwave techniques.

Heterodyne mixers beat the signal RF frequency against a known local oscillator (LO) frequency to generate an intermediate frequency (IF) difference signal that is tunable through the LO frequency. The LO can have a fixed output power that is generally much greater than the power of the received RF signal. A nonlinear mixer produces an IF output power that is proportional to the product of the powers of the received RF signal and the LO signal. Mixers display good rejection of incoherent noise and interference. They are typically fast, with IF bandwidths of 0.1 to 10 GHz. Furthermore, narrowband detectors do not require additional frequency selective elements to analyze the spectrum of the incoming terahertz radiation as long as the received RF signal is within an IF bandwidth of the LO frequency. Therefore, heterodyne detectors have been used in narrow frequency band, high-resolution applications at lower terahertz frequencies, such as for molecular spectroscopy. Common mixers are field-type devices that have a strong quadratic nonlinearity.

Only within the last several years has the possibility of an all solid-state infrastructure for photonics at THz frequencies become a realistic possibility. This possibility has been primarily due to the invention and continued development of miniature semiconductor QCLs. Such QCLs are the only coherent solid-state source that can output the many milliwatts of average THz power necessary to transmit through the atmosphere and to supply sufficient LO power to THz diode receivers, with the goal of replacing the gas- and vacuum-tube THz sources most commonly used today. To date all reported THz photonic systems employing QCLs have used discrete source and detector components coupled via mechanically aligned free-space quasioptics, where coupling losses and system size pose significant impediments to practical use. To reach the same maturity level as existing infrared/visible photonics requires integration of solid-state THz sources, detectors, and auxiliary passive and active functionalities onto a compact, chip-based platform amenable to microfabrication methods.

Therefore, a fast solid-state terahertz radiation mixer is still needed to enable coherent detection for terahertz applications. In particular, a microelectronic-based integrated heterodyne terahertz transceiver is highly desirable for field-deployable applications. Such a transceiver requires the successful integration of both terahertz sources and detectors on a single chip, along with cooling, optics and control electronics, while maintaining high source power (e.g., greater than 10 mW), detection sensitivity, and operating temperatures, all in a compact, reliable, integrated package.

SUMMARY OF THE INVENTION

The present invention is directed to an integrated heterodyne terahertz transceiver, comprising a quantum cascade laser having a bottom contact layer, a layered heterostructure of two or more semiconductor alloys on the bottom contact layer, and a top waveguide layer on the layered semiconductor heterostructure, thereby providing an active semiconductor core between the top and bottom layers; and a Schottky diode comprising a rectifying metal contact on the top surface of the layered semiconductor heterostructure, wherein the quantum cascade laser couples terahertz local oscillator power to the Schottky diode to mix with a received terahertz signal to provide an intermediate frequency output signal. The received terahertz signal can be coupled to the transceiver through an antenna connected to the Schottky diode, through an end facet or sidewall of the semiconductor core, through a portion of the waveguide, or through an active section that intersects the laser. Alternatively, the transceiver can be used as a power meter by responding to the signal directly, without mixing with the local oscillator.

The fully integrated transceiver optimizes power efficiency, sensitivity, compactness, and reliability. The transceiver can be used in compact, fieldable systems covering a wide variety of deployable applications not possible with existing technology.

For example, the transceiver can be used for high-specificity, real-time point detection. Especially at low pressures, terahertz signatures of many molecules are very unique, enabling identification even with only a few spectral lines over a narrow spectral region. Thus in accessible areas, compact point sensors based on terahertz signatures can be very specific tools for identifying many important compounds. These point sensors can form a sniffer system used to monitor emissions from facilities to portals to look for materials, such as explosives. The narrow linewidth of the local oscillator combined with the resolution of the heterodyne mixer yields very high specificity in this type of application.

The transceiver can also be used for high-specificity, real time, passive detection. With existing terahertz components integrated into a heterodyne transceiver, passive remote detection is possible from radiative emission of gases hot with respect to the background or absorption by gases backlit by hotter backgrounds. This enables, for example, identifying effluent emissions from exhaust stacks, and byproducts of explosions or fuel combustion. Without heterodyne detection the thermal background would prevent success in these types of environments.

The transceiver can also be used for high-specificity, real time, active detection. Active remote sensing can be utilized, for example, via differential absorption laser spectroscopy (DIAL). With DIAL, temperature differences are not required for detection and range is limited by source power and backscatter cross-section. This can be used for short-range portal applications, looking through materials such as clothing or packaging materials for reflection as well as emission spectra, to mid-range applications of discriminating chemical and biological agents in a cloud, to multi-km range exoatmospheric radar type applications. The heterodyne/homodyne nature of the detection using a transceiver is essential for these applications by increasing signal-to-noise of the measurement by orders of magnitude compared to direct detectors combined with a separate laser source.

The transceiver can be used as a high-resolution spectroscopy tool for enhanced signature development. The transceiver enables higher resolution spectroscopy over a differential frequency range determined by the bandwidth of the mixer detector centered on a sharply defined terahertz laser frequency. Terahertz QCLs have narrower linewidths than the Doppler-limited linewidth of 1 MHz (in the THz), which is significantly better resolution than Fourier-Transform Infrared (FTIR) methods (about 60 MHz). Especially for heavier molecules, this QCL-limited linewidth enables cataloguing features otherwise unobservable with FTIR spectroscopy, which is critical for accurate modeling and assignment of remotely measured signatures.

The transceiver can be used for broad-band spectroscopy. Typically, laser spectroscopy is performed by using a tunable single frequency laser and a broadband detector. To be able to identify more than one molecule, it is preferred that the laser be broadly tunable. Adding a distributed-feedback (DFB) grating to a THz QCL so that it emits at a single frequency typically limits the tuning to less than 10 GHz, thus limiting spectroscopy. However, QCLs generally have a broad gain-bandwidth which allows them to be tuned over at least a few hundred GHz. With the DFB, the laser can emit into a collection of modes spanning over 300 GHz simultaneously, but this characteristic is typically not used for spectroscopy since incoherent detectors measure the power of all the modes combined and cannot separate the power in each mode. Since the heterodyne receiver measures the power at specific frequencies, two multi-moded QCLs (where at least one has a integrated diode) can be used to measure multiple tunable lines simultaneously. Thus, if the current of only one of the lasers is swept all of its lines will sweep frequency and by mixing these lines against the lines in the receiver, the power fluctuations of each line can be monitored independently. This enables spectroscopy over a much broader frequency range when tuning the laser with current or temperature than a single frequency QCL illuminating a direct detector.

The transceiver can be used to as a diagnostic tool to monitor internal laser characteristics. The DC current-voltage relation for the diode changes with the laser intensity and therefore can be used as an internal power meter. Also, if enough current is pumped through a QCL it can switch from single-mode operation to multi-mode operation, and the diode can detect when this happens since a heterodyne beat signal due to the internal modes will occur once there are two or more modes. The receiver response can be used to monitor sensitivity to feedback to emitted light that gets reflected back into the laser. The feedback can also be used for vibrometry or as a "radar gun" at higher frequencies. For example, the vibration frequency of objects that reflect light back into the QCL can be measured. Similarly, the Doppler shift of moving objects can be measured in the THz regime.

BRIEF DESCRIPTION OF THE DRAWINGS

The accompanying drawings illustrate the present invention and, together with the description, describe the invention. In the drawings, like elements are referred to by like numbers.

FIG. 3 is a top-view schematic illustration of an integrated heterodyne terahertz transceiver comprising a Schottky mixer on top of a QCL ridge structure and a separate active section for amplifying the incident received terahertz signal.

FIG. 7A is the Fourier transform spectrum of the QCL transmission, showing ten longitudinal mode peaks of varying intensities spaced at approximately 13 GHz intervals around 2.8 THz. FIG. 7B is the spectrum recorded on a microwave spectrum analyzer that shows the intermediate frequency (IF) signal from the diode.

FIGS. 8A-B show the IF spectra resulting from the heterodyne reception of a difluoromethane $CO_2$-pumped molecular gas laser signal. FIG. 8C shows how the IF signal lines are generated as difference frequencies between the molecular gas line and the QCL's F-P mode lines.

FIG. 10A is a schematic illustration of the experimental setup. FIG. 10B is a plot of the IF spectrum of a phase locked integrated transceiver.

DETAILED DESCRIPTION OF THE INVENTION

Figure 1:
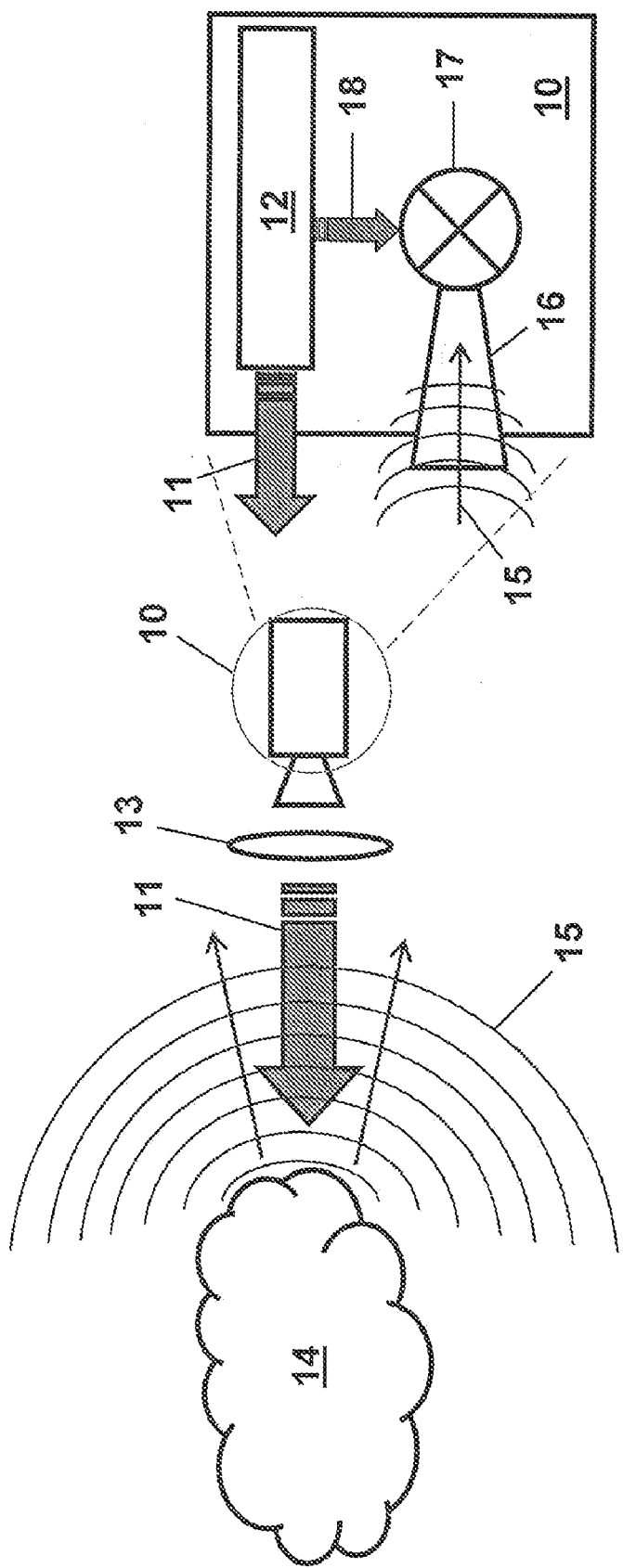
FIG. 1 is a schematic illustration of an active remote sensing system comprising a heterodyne terahertz transceiver.

In FIG. 1 is shown a schematic illustration of an active remote sensing system comprising a heterodyne terahertz transceiver 10 that combines a terahertz transmitter with a terahertz receiver. The transceiver 10 transmits terahertz radiation 11 from a terahertz source 12 at a known frequency. The terahertz radiation 11 can be controlled by optics 13 to illuminate a remote object, or target 14. A return terahertz signal 15 is radiated from the target 14 and is collected by the optics 13 and detected by the transceiver 10. The returned signal 15 can be received by a horn or antenna 16 and coupled to a mixer 17 of the transceiver 10. The mixer 17 can comprise a Schottky-type diode (for heterodyning, the Schottky diode is referred to herein as a mixer). A portion of the transmit power is coupled from the terahertz source 12 to the mixer 17 as a LO 18 to define a detection frequency reference. An IF circuit (not shown) processes the mixer output. The mixer 17 therefore detects terahertz radiation within a limited bandwidth around the LO frequency and is insensitive to signals at frequencies outside this bandwidth, thereby rejecting noise outside the detection bandwidth.

The present invention is directed to an integrated heterodyne terahertz transceiver that uses the monolithic integration of a THz QCL and a solid-state THz mixer to form a simple but generically useful THz photonic integrated circuit. This transceiver embeds a small Schottky diode into the ridge waveguide cavity of a QCL, so that LO power is supplied to the diode's cathode directly from the QCL's internal fields with no optical coupling path for the LO. This THz photonic integrated circuit performs all the basic functions (e.g., transmission of a coherent carrier, heterodyne reception of an external signal, frequency locking and tuning) of discrete component THz photonic systems, but at a small fraction of the size and in a robust platform scalable to semiconductor fabrication production.

When an electromagnetic field is coupled to the Schottky diode (the point contact), a change in the low frequency electrical response is observed due to the rectifying nature of the point contact. If the field amplitude remains constant in time this change will remain constant in time. If two fields are coupled to the mixer, the instantaneous field amplitude will be modulated in time. This modulation occurs at the difference, or intermediate frequency due to the superposition of the two fields. This IF signal can be measured, for example with a spectrum analyzer. If one of the fields that is created by the QCL is defined as the LO, the frequency of all other fields incident on the transceiver can then be determined "simultaneously" by sweeping the spectrum analyzer.

Figure 2:
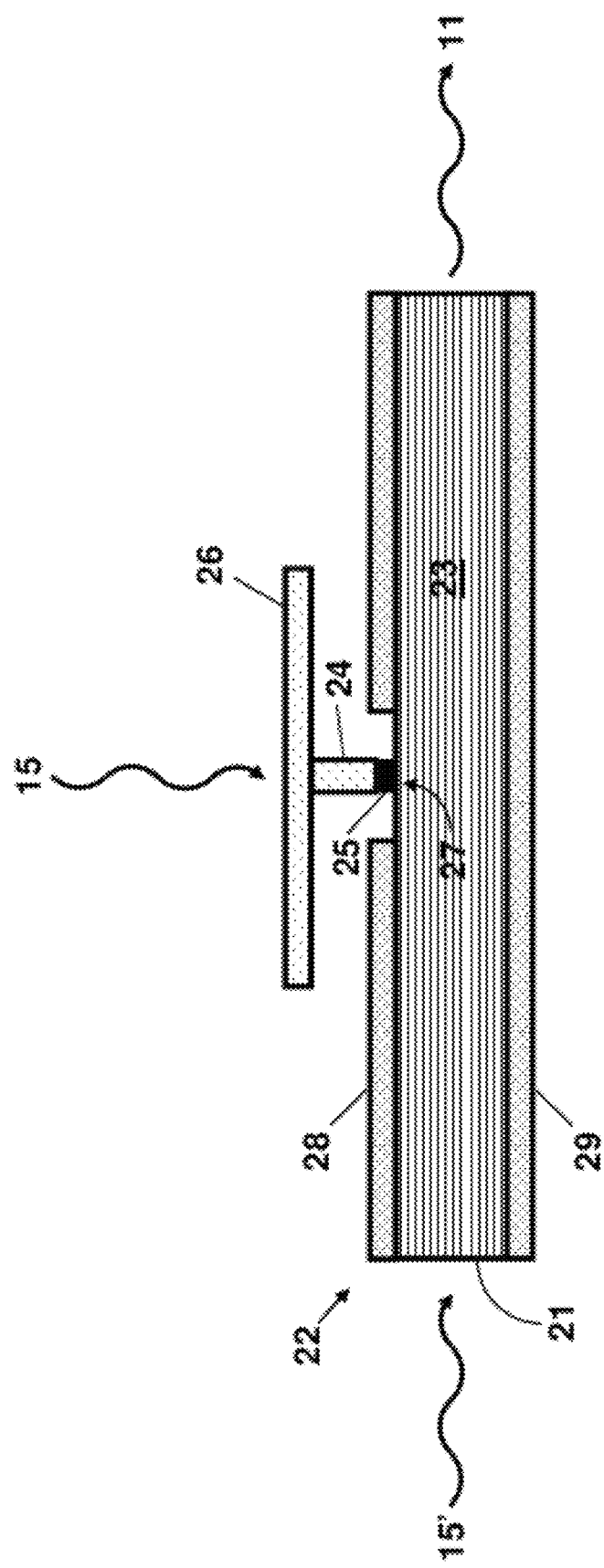
FIG. 2 is a side-view schematic illustration of an integrated heterodyne terahertz transceiver. The terahertz source portion of the transceiver comprises of a terahertz QCL structure. The terahertz heterodyne mixer portion of the transceiver comprises a Schottky-type diode (i.e., metal-to-semiconductor contact diode) that is directly integrated with the QCL structure and draws its LO frequency reference from the internal electromagnetic field in the QCL structure.

In FIG. 2 is shown a side-view schematic illustration of an exemplary embodiment of the integrated heterodyne terahertz transceiver of the present invention. The transceiver integrates onto a single semiconductor chip platform a terahertz QCL 22 and a single or an array of Schottky diode mixers 27. The QCL 22 supplies the LO source for the mixer 27 and also, if needed, a coherent active illumination source 11. When the QCL 22 is used as an active illumination source, the mixer 27 can phase lock onto the LO, yielding extremely high rejection of background interference.

The QCL 22 comprises a layered heterostructure of two or more semiconductor alloys forming an active semiconductor core 23 between a top waveguide layer 28 and a bottom contact layer 29. The design of the heterostructure can vary, depending on the transceiver requirements. Typically, the active region in the heterostructure is repeated many times until the stack thickness is about ten microns, although thicker or thinner stacks can also be used. For example, the heterostructure can comprise alternating thin layers of GaAs and AlGaAs. The heterostructure can be built up by MBE on a semi-insulating (SI) gallium arsenide substrate. Such GaAs/AlGaAs heterostructures can typically operate in a range of about 2.0 to 4.5 THz. However, other heterostructure designs and other semiconductor alloys can be used to build up heterostructures that operate at other terahertz frequencies. See R. Kohler et al., "Terahertz semiconductor-heterostructure laser," *Nature* 417, 156 (2002), which is incorporated herein by reference.

The top and bottom layers 28 and 29 are typically metal or doped-semiconductor layers that keep the mode in the laser cavity. In particular, with terahertz QCLs the mode is confined by interaction with a surface plasmon at the semiconductor/metal interface. The waveguide layers can also provide electrical contacts to the semiconductor core 23. In the embodiment shown here, the Schottky diode 27 can be the small interface between the semiconductor core 23 and a metal 25. To make a diode, the metal 25 at this interface must be rectifying. For example, titanium makes a particularly stable Schottky contact to a GaAs-based semiconductor core. The layers 28 and 29 over the rest of the semiconductor core 23 can be a different metal that preferably provides an ohmic contact to the semiconductor material, rather than a rectifying contact. Typically, a combination of metals can be used to make the ohmic contact. For example, metal stacks of nickel, gold, and germanium, or palladium, germanium, and gold, can be used to make ohmic contacts to GaAs-based semiconductor materials. The waveguide thicknesses can be one-micron or less, although a thicker bottom layer can be used to bond the laser to another metal for heat sinking.

Various means can be used to couple the incident radiation into the transceiver. Regardless of the means for coupling the incident radiation to the transceiver, the LO power is coupled directly to the mixer, due to the intrinsic properties of the terahertz QCL. In the example shown in FIG. 2, the incident terahertz signal 15 is focused onto an antenna 26 which couples it to the mixer 27. A metal post 24 can connect the rectifying metal 25 to the antenna 26 for receiving the incident radiation 15. Many metals can be used in the post 24 and antenna 26, so long as they do not affect the Schottky contact 27. The antenna 26 preferably has a low surface resistance and is structurally rigid. For example, gold can be used to provide the desired antenna properties. A palladium-gold or platinum-gold alloy can cover the diode to prevent diffusion to the titanium contact. A variety of antenna or horn configurations can be used. In FIG. 2 is shown a patch antenna. For example, the patch antenna can be approximately 50 microns square and a couple microns in thickness. A dipole antenna, or post extending vertically above the surface, either perpendicular to the surface or at an angle, can also be used. Focused ion beam deposition can be used to make or attach a nearly vertical antenna, although other methods, such as laser-assisted chemical vapor deposition or deep lithograph and plating, can also be used.

If the incident THz radiation is coupled to the diode through active material, the input beam can be amplified. Therefore, as shown in FIG. 2, incident THz radiation 15' can be coupled in through an end facet 21 or a side of the laser 22. Coupling the power in through a facet may enable pre-amplification of the input signal in the photonic domain in active material before coupling to the diode. Since the amplification would be via stimulated emission and hence coherent with the signal, it may enable lower-noise amplification than RF amplification after the signal is mixed into the RF electronics domain.

The incident radiation can also be coupled through a separate active amplifier material section that intersects the laser. In FIG. 3 is shown a top-view schematic illustration of an integrated heterodyne terahertz transceiver comprising a Schottky mixer 27 on top of a QCL ridge structure and a separate active section 37. The ridge structure provides the laser cavity of the QCL 22. The ridge structure and separate amplifier section can be formed on a substrate that also provides a bottom electrical contact and waveguide layer. A high-frequency lead 35 to the mixer 27 can bring the IF signal off the chip. Coupling the incident terahertz radiation 15" through the separate active section 37 can have several benefits. First, in can prevent feedback effects or frequency pulling of the laser. Second, the amplifier section can be optimized separately without affecting the laser performance. For example, if a distributed feedback (DFB) grating is applied to the laser to ensure single mode operation, the grating would prevent all but a few frequencies from propagating inside the laser waveguide. The amplifier section can be made without the DFB grating and therefore would allow reception of incident radiation over a broad frequency range. Even without a DFB grating, the laser cavity will tend to amplify different frequencies by different amounts. With appropriate design (and possible antireflection coatings) cavity effects on the amplifier can be eliminated so that the amplification is less frequency dependent.

Figures 4A, 4B:
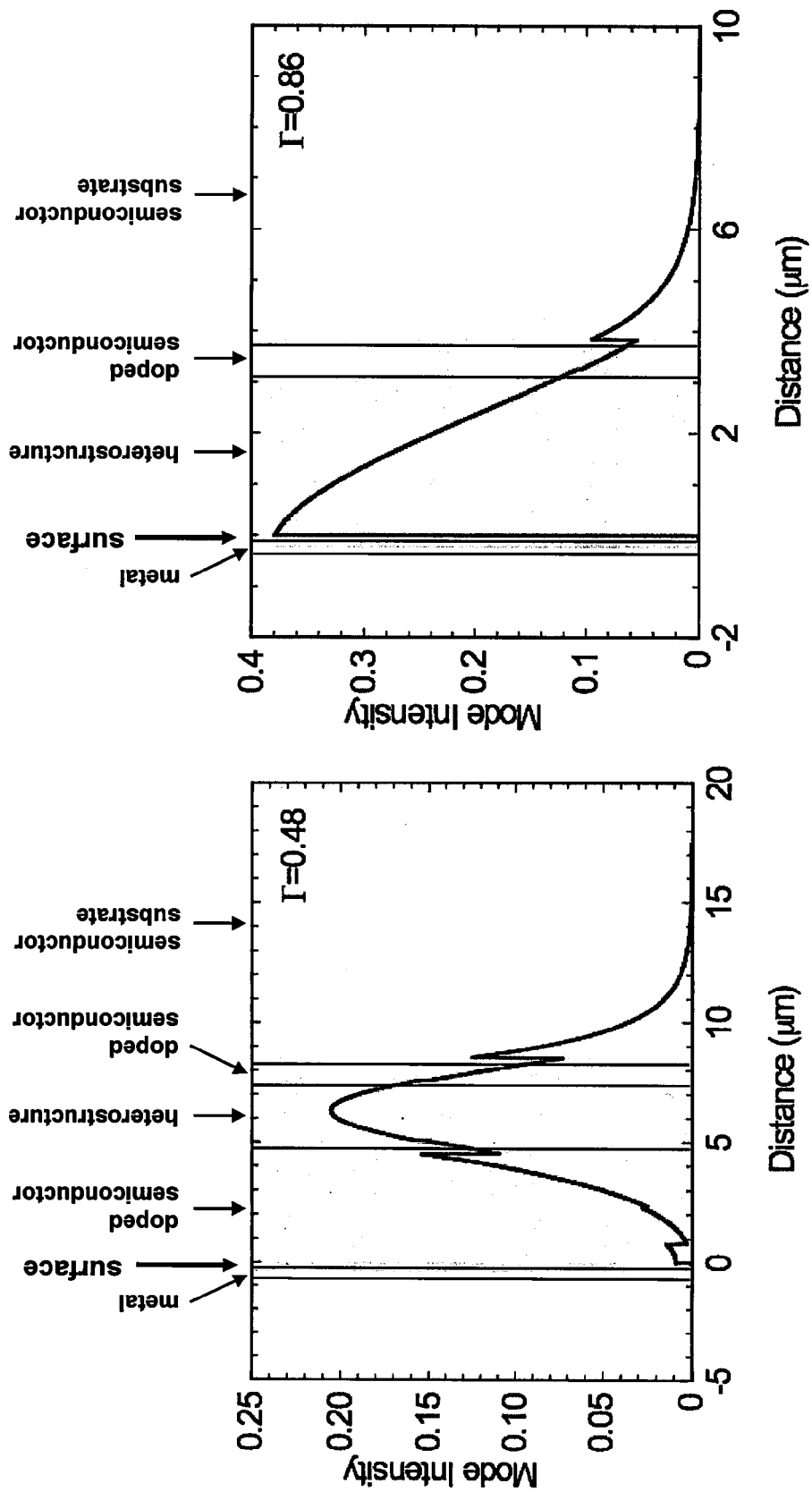
FIG. 4A shows the spatial dependence of the laser field intensity inside the laser cavity for a standard shorter wavelength semiconductor laser.
FIG. 4B shows the spatial dependence of the laser field intensity inside the laser cavity for a terahertz QCL comprising a metal/semiconductor waveguide.

In FIGS. 4A and 4B are shown the spatial dependences of the laser field intensity inside the laser cavity formed by the active semiconductor core, for standard shorter wavelength semiconductor lasers and a terahertz QCL, respectively. In these figures, the top metal-waveguide-layer/semiconductor interface is on the left. As shown in FIG. 4A, the field intensity near the surface is very weak for the standard semiconductor laser. However, as shown in FIG. 4B, the field intensity of a terahertz QCL peaks at the surface and enables the integration of the QCL with the Schottky diode. Therefore, the field is high at the metal/semiconductor interface defining the Schottky diode and coupling of the LO from the terahertz QCL is achieved without the use of an antenna. See R. Sachs and H. G. Roskos, *Optics Express* 12, 2062 (2004); O. Demichel et al., *Optics Express* 14, 5335 (2006); S. Kohen et al., *J. Appl. Phys.* 97, 053106 (2005); and Q. Hu et al., *Semicond. Sci. Technol.* 20, S228 (2005), which are incorporated herein by reference.

Figure 5A:
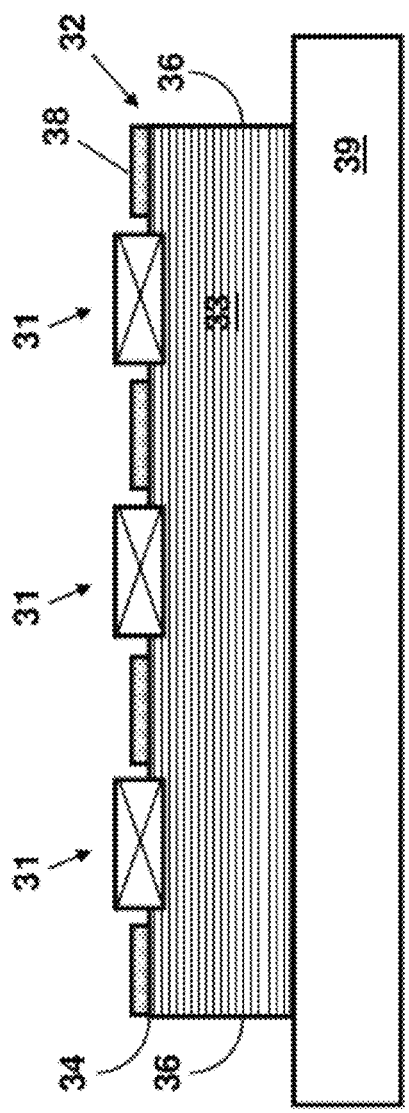
FIG. 5A shows a side-view schematic illustration of an integrated heterodyne terahertz transceiver comprising an array of receivers.
Figure 5B:
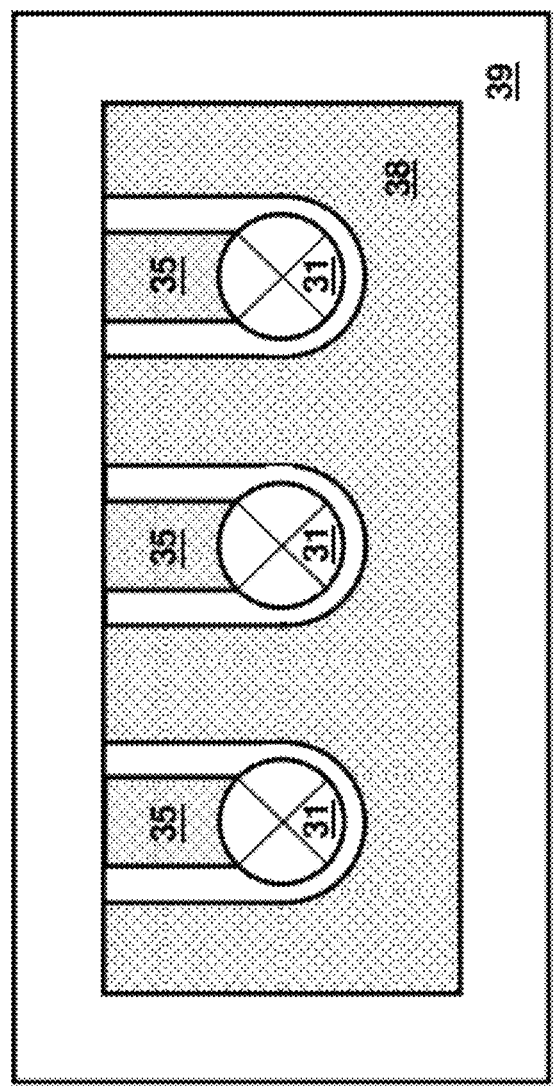
FIG. 5B shows a top-view schematic illustration of the transceiver.

In FIG. 5A is shown a side-view schematic illustration of another embodiment of the integrated heterodyne terahertz transceiver comprising an array of three separate terahertz receivers 31 on top of a semiconductor core ridge structure 33. The ridge structure 33 provides the laser cavity of the QCL 32. A typical ridge structure is 30- to 400-µm wide and one to a few millimeters long. The ridge structure 33 can be formed on a substrate 39 that provides a bottom electrical contact and waveguide layer. For example, a GaAs-based heterostructure can be built on a GaAs substrate. Alternatively, the QCL can be bonded to a metal layer on a GaAs substrate, or directly to a metal that has the same thermal expansion coefficient as the semiconductor core material (e.g., tungsten-copper for a GaAs-based core). An array of holes is formed through the QCL's top electrical contact and waveguide metallization 38 to expose the underlying semiconductor. Each receiver 31 comprises a separate mixer 27. Each receiver can have a separate antenna or the incident radiation can be received by one of the other coupling means described above. Each receiver 31 can be monolithically fabricated or flip-chip bonded to the exposed top surface of the ridge structure 33 to form the metal-to-semiconductor contact of the Schottky diode mixer 27. The size of the diode mixer and the hole will depend on the frequency of the laser, but can typically be about one-tenth micron and a couple microns, respectively. The spatial strength of the field inside the laser cavity peaks at the top surface 34 of the ridge structure 33. The mixer portion of the receiver 31 can be flush with or protrude into the propagating terahertz field inside the ridge structure 33, so that a small fraction of the internal terahertz field can be drawn off to supply the LO power to the mixer. Since the difference IF signal can be any frequency up to the bandwidth of the mixer (e.g., DC to 40 GHz or higher), high-frequency leads can bring the IF signal off the chip. As shown in FIG. 5B, this high-frequency lead 35 can comprise a coplanar waveguide (CPW) for each receiver 31. For example, the CPW can comprise gold. Alternatively, other types of high-frequency leads, such as a microstrip line or high-frequency waveguide can be fabricated lithographically on top surface of the QCL ridge cavity.

When operated in an active mode, the transceiver's target illumination signal can be broadcast from an end facet 36 of the QCL cavity 33. Typically, the end facet 36 can be the cleaved end of the QCL bar, but the end can also be etched. With plasmon waveguided laser cavities, the reflectivity of a cleaved end facet is about 30%. With a metal-metal waveguide, the reflectivity can be higher, for example, 85%. The return signal from the target can be received by an antenna connected to the metal anode of the mixer diode of each receiver 31 or through an end facet or one of the other coupling means described above. Alternatively, if the target passively radiates its own light and the transceiver is only needed to operate as a heterodyne receiver, high-reflectivity facets can be formed on the end facets of the laser, further increasing the device efficiency and maximum operation temperature. For example, the reflectivity of the end facets can be increased by applying an insulator to a cleaved end facet and covering them with a gold layer. In either the active or passive mode, supplying the LO power to the mixer in this integrated method differs from the conventional method of simply shining light from a QCL's facet output onto the mixer, either through a free-space or an on-chip waveguide. Because this internal terahertz field is larger than the terahertz field exiting the output facet of the laser, this integrated method of delivering LO power to the mixer has advantages in power efficiency, compactness, simplicity, and flexibility of design over conventional methods of supplying LO power to the mixer.

Finally, because the mixer is embedded in the laser semiconductor core, the transceiver can be used as an internal diagnostic to monitor the QCL performance itself. For example, the mixer can act as a power meter when the laser is running single mode, and will indicate a heterodyne beat signal if the laser starts running multi-mode. Since single-mode operation is important for many of the above applications, being able to confirm that the laser is running single mode is a great advantage.

Integrated Heterodyne Terahertz Transceiver Example

Figure 6:
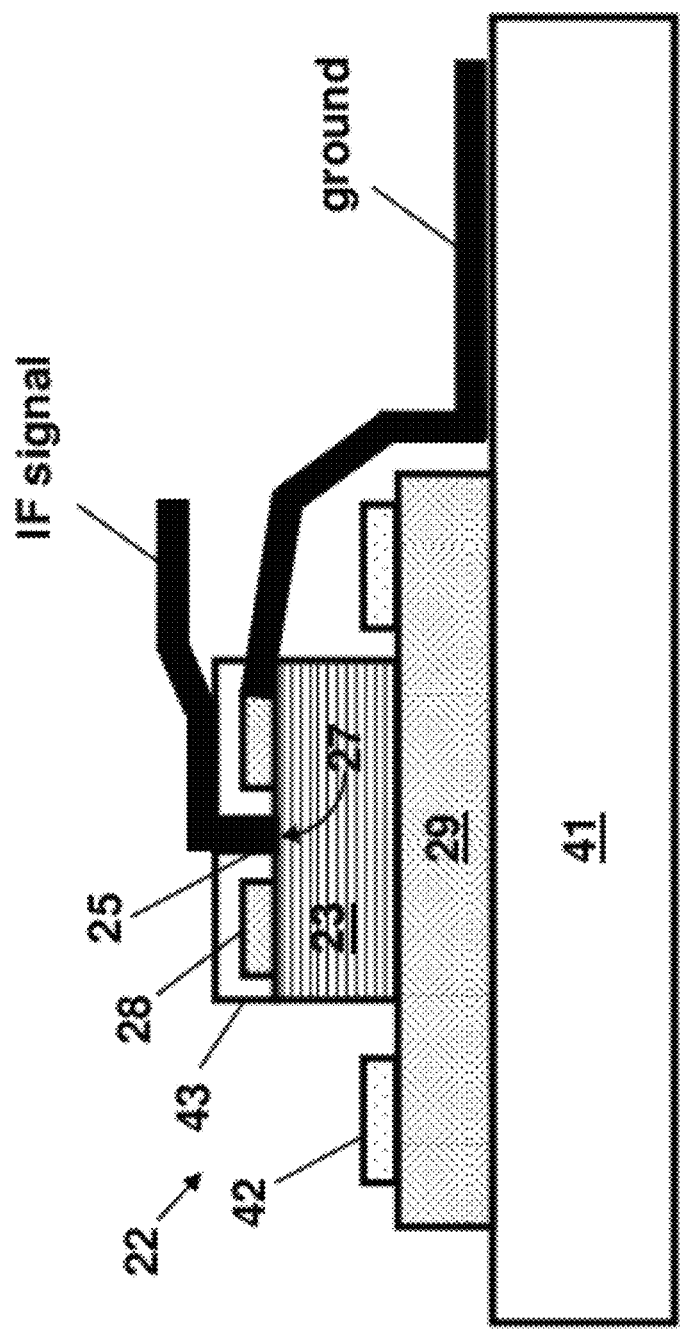
FIG. 6 is an end-view schematic illustration of an exemplary integrated heterodyne terahertz transceiver.

An exemplary integrated heterodyne terahertz transceiver was fabricated and tested to demonstrate the present invention. FIG. 6 shows an end-view schematic illustration of the exemplary transceiver. The exemplary transceiver comprised a metal-semiconductor Schottky diode mixer 27 that was directly fabricated onto a THz QCL 22. The QCL comprised a bottom ohmic contact layer 29 that was formed on a GaAs substrate 41. Bias could be applied to the QCL through bond pads 42 attached to the bottom contact layer 29. For this demonstration, the RF signal was coupled into the transceiver through an end facet of the QCL, rather than through an antenna. The semiconductor cathode of the Schottky diode and the top bias contact of the QCL ridge waveguide shared the same n+ doped GaAs layer of the semiconductor core 23. A less than 1 µm diameter Ti/Au metal anode 25 was fabricated on the n+ GaAs to define a Schottky contact, while an ohmic contact 28 was formed over the remaining area of the n+ GaAs layer to form the negative (ground) contact for both laser and diode. A dielectric stack 43 covered the top waveguide layer 28.

This integration strategy has the advantage that the QCL ridge waveguide cavity's internal electric field permeates the diode's cathode and is strongest near the metal-semiconductor interface of the Schottky contact. The internal field is correctly polarized to drive high-frequency currents across the metal-semiconductor contact and hence modulate the diode's depletion region width. In addition, the power in the internal THz field is roughly 50% greater than the laser's externally radiated power in a plasmon guided QCL, and over ten times greater in a metal-metal guided QCL. In this way, the QCL supplies LO power to the integrated Schottky diode mixer in an efficient and physically compact manner, eliminating the need for optical alignment between a separate source and mixer components. The Schottky diode, if sufficiently small, can be fabricated successfully without significantly degrading the QCL's lasing characteristics.

This photonic integrated circuit operates as both a coherent THz transmitter and as a heterodyne receiver of external THz signals having frequencies within roughly ±25 GHz of a QCL mode line. Finally, the integrated diode acts as a very sensitive and high precision probe of the electrodynamics within the QCL resonant cavity. An internally generated signal from this probe can be used, for example, to monitor subtle QCL Fabry-Perot mode frequency shifts in response to changing external conditions, and as feedback to phase lock the modes of a multimode QCL and achieve exceptional differential mode stability.

Fabrication of the exemplary integrated transceiver began with MBE growth of a 2.8 THz plasmon waveguided QCL following a design described by Barbieri et al., *Appl. Phys. Lett.*, 85(10), 1674 (2004), which is incorporated herein by reference. The transceiver comprised an array of Schottky diodes and associated contacts that were integrated as follows. A SiN/SiO/SiN dielectric stack 320 nm thick was deposited on the QCL material, and e-beam lithography defined 1 µm diameter openings for the Schottky diodes. A reactive ion etch cleared the dielectric stack in the openings down to the GaAs contact, and a Ti/Au (20/100 nm) Schottky anode was sputter deposited to fill the openings. The Schottky metal on the dielectric was then etched to 4 µm diameter circles, and the exposed dielectric stack etched away. Liftoff was used to produce 165 µm wide ohmic contacts to the top surface of the QCL waveguide, with a 7 µm diameter opening in the metal around the Schottky diode. Subsequently, another dielectric stack was deposited over the ohmic contact, and openings etched through it for access to ohmic and Schottky metals. Mesas 170 µm wide were created using a $Cl_2/BCl_3$ plasma to etch away the material around the top metal stripe down to the lower n+ contact layer. Liftoff defined the lower contact metal, and the sample was annealed at 380° C. for 30 seconds to obtain low contact resistance. A second etch was used to remove the lower n+ layer beyond the bottom contacts metallization (starting 95 microns from either side of the laser stripe) to provide a low loss substrate for the high-frequency CPW used to bring the mixer signal off the chip. Another silicon nitride layer was deposited over the structure, with openings etched through it to access the upper and lower ohmic laser contacts and the Schottky diode. A photoresist structure was patterned and reflowed to provide a dielectric bridge from the upper contact and Schottky contact down to the substrate level. Gold was plated to provide a 50Ω impedance CPW to the Schottky metal, and to bridge from the upper and lower ohmic contacts to wire bond pads. Finally, the wafer was thinned to 250 μm to improve thermal conduction and cleaved into 3 mm long bars.

The QCLs were cleaved long enough to ensure multimode operation with Fabry-Perot (F-P) mode spacings close to 13 GHz. This allowed the diagnosis of whether the integrated diode coupled properly to the laser by observing the 13 GHz signal from the mixing of periodically spaced internal modes of the laser. The on-wafer 50Ω CPW was used to access this signal. The center conductor of the CPW was connected to the diode anode and the ground traces were connected to the diode cathode, which was also the QCL ground. Minimizing the feed capacitance was not essential because the capacitance provided the THz signal return for the currents generated at the detector anode back to the laser top contact. The CPW started on top of the laser ridge, was air bridged over the lower contact, and then ran along the substrate to bond pads. The integrated transceiver was wire bonded into a fixture with SMA connectors to maintain a 50 ohm transmission line all the way from the diode to the external RF measurement equipment. The resulting bandwidth of the microwave test interface was greater than 20 GHz.

Post-integration, the DC current-voltage (I-V) characteristic of each diode was measured to confirm a Schottky contact was formed. The diode I-Vs typically showed an ideality factor n≈1.9, and total series resistance around 140Ω. The lasing characteristics of the QCLs were also measured after integration processing and still showed robust THz emission after integration of the diodes with no measurable change in lasing threshold bias conditions. With the QCLs lasing, diode I-Vs showed a DC offset from rectification of the THz field, indicating the diodes were coupling to the internal fields of the QCLs.

Figure 7A:
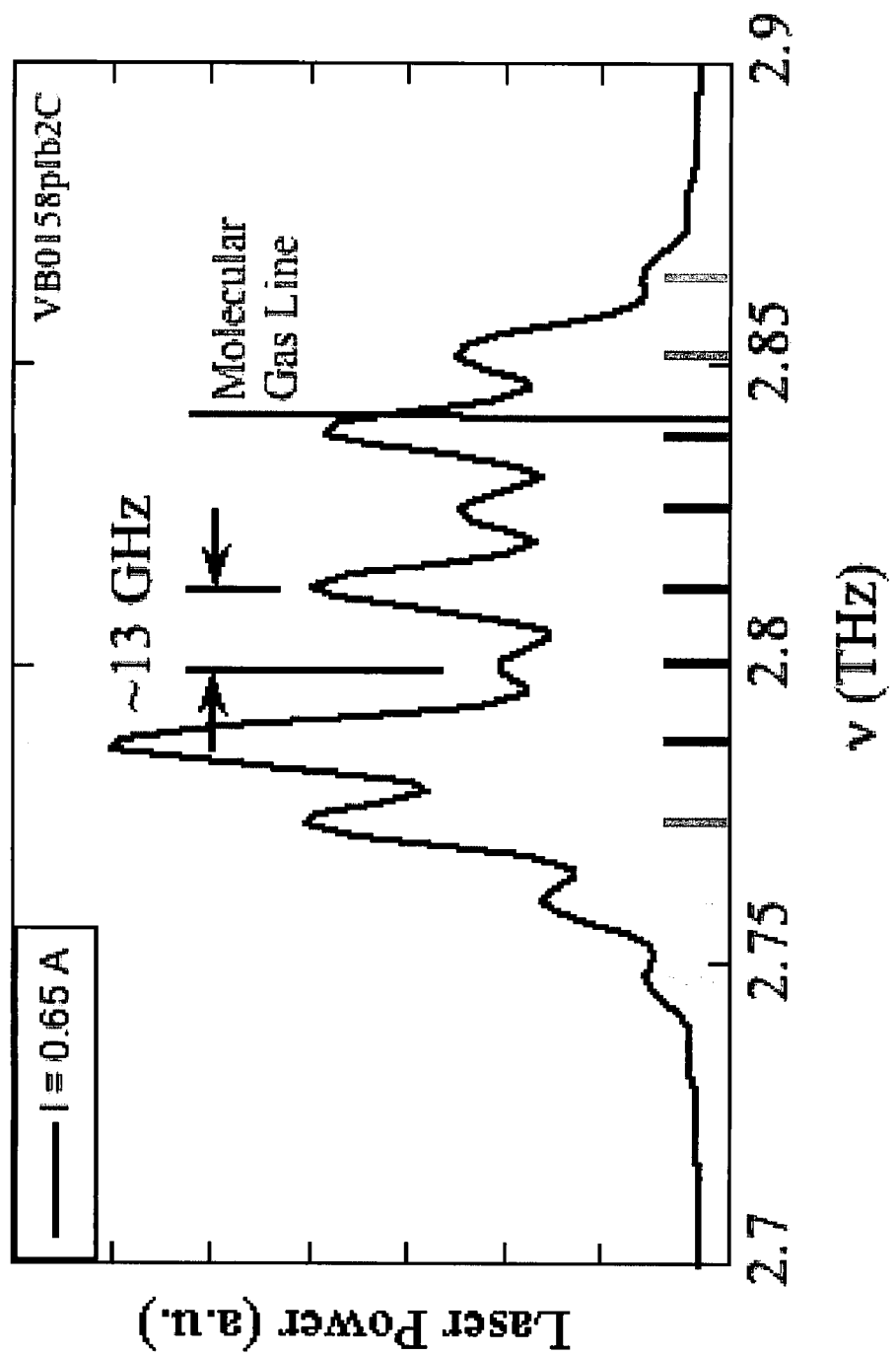
FIGS. 7A-B are plots that demonstrate coupling to and mixing of the Schottky diode with the internal fields of the QCL of an exemplary integrated heterodyne terahertz transceiver.
Figure 7B:
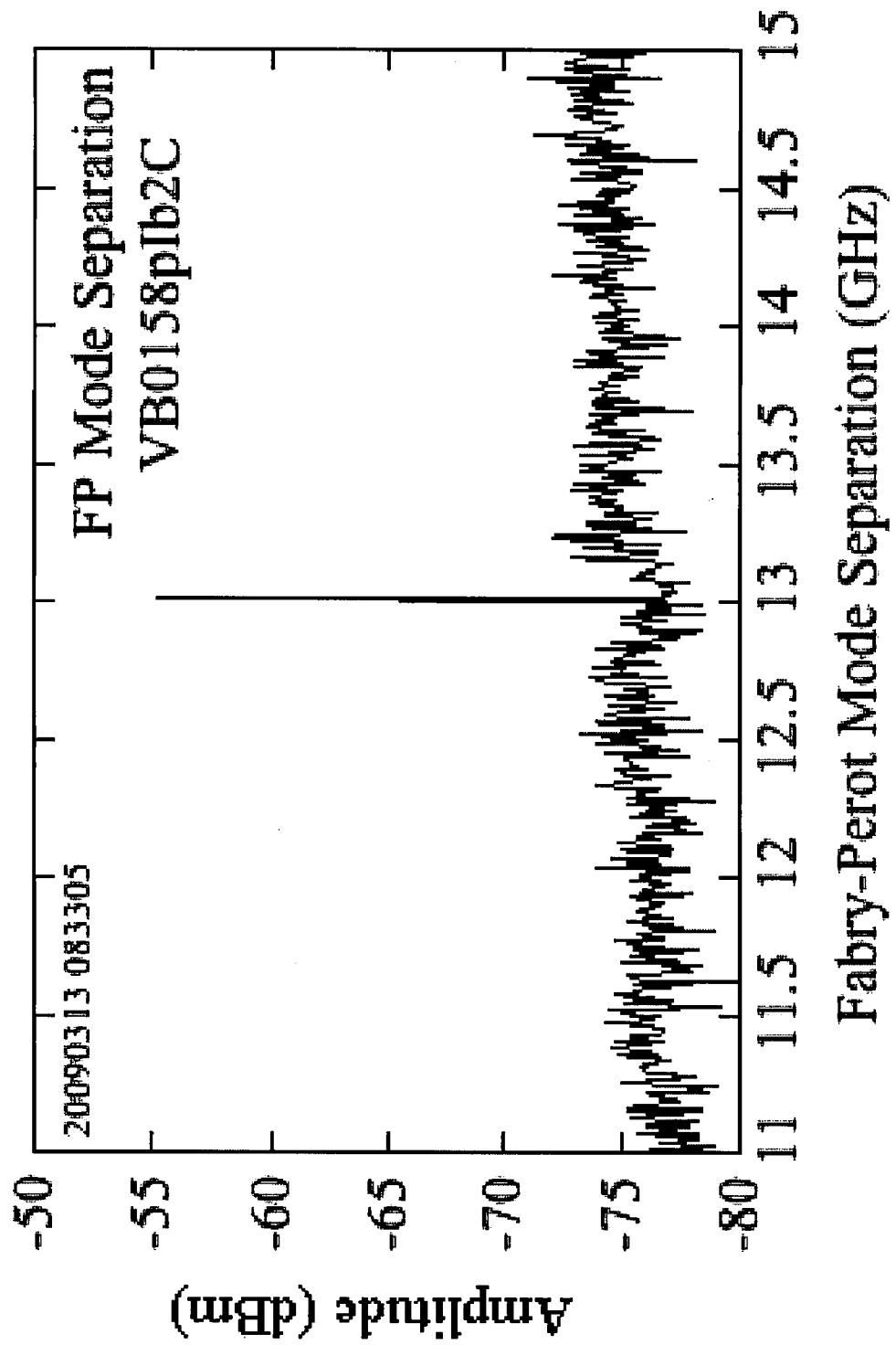

FIGS. 7A-B demonstrate that the integrated diodes were coupling to and mixing the internal fields of the QCLs. The QCL for this integrated transceiver was biased at 0.65 A/3.5 V to run multimoded, while the diode was operated unbiased. The transceiver was cooled in a liquid helium flow cryostat to an operating temperature near 10 K. As shown in FIG. 7A, the Fourier transform spectrum (FTS) of the QCL transmission showed ten longitudinal mode peaks of varying intensities spaced at approximately 13 GHz intervals around 2.8 THz. 13 GHz was the calculated spacing between Fabry-Perot modes given the emission frequency, laser cavity index, and QCL length. The FTS also showed that the intermode spacing decreased slightly with increasing temperature. As shown in FIG. 7B, the IF signal from the diode that was recorded on a microwave spectrum analyzer without using an IF amplification chain. With the laser free-running in multimode operation, a clear IF signal peak at 12.961 GHz was observed from the diode's output. This IF signal represents the difference frequency between the laser modes generated by heterodyne down conversion at the diode. The spectral width of the IF signal in the free running laser may be due to small variations in the precise mode spacing between different adjacent modes of the QCL. However, the appearance of this mixing signal clearly shows that the integrated diode responds to 2.8 THz fields.

Figure 8A:
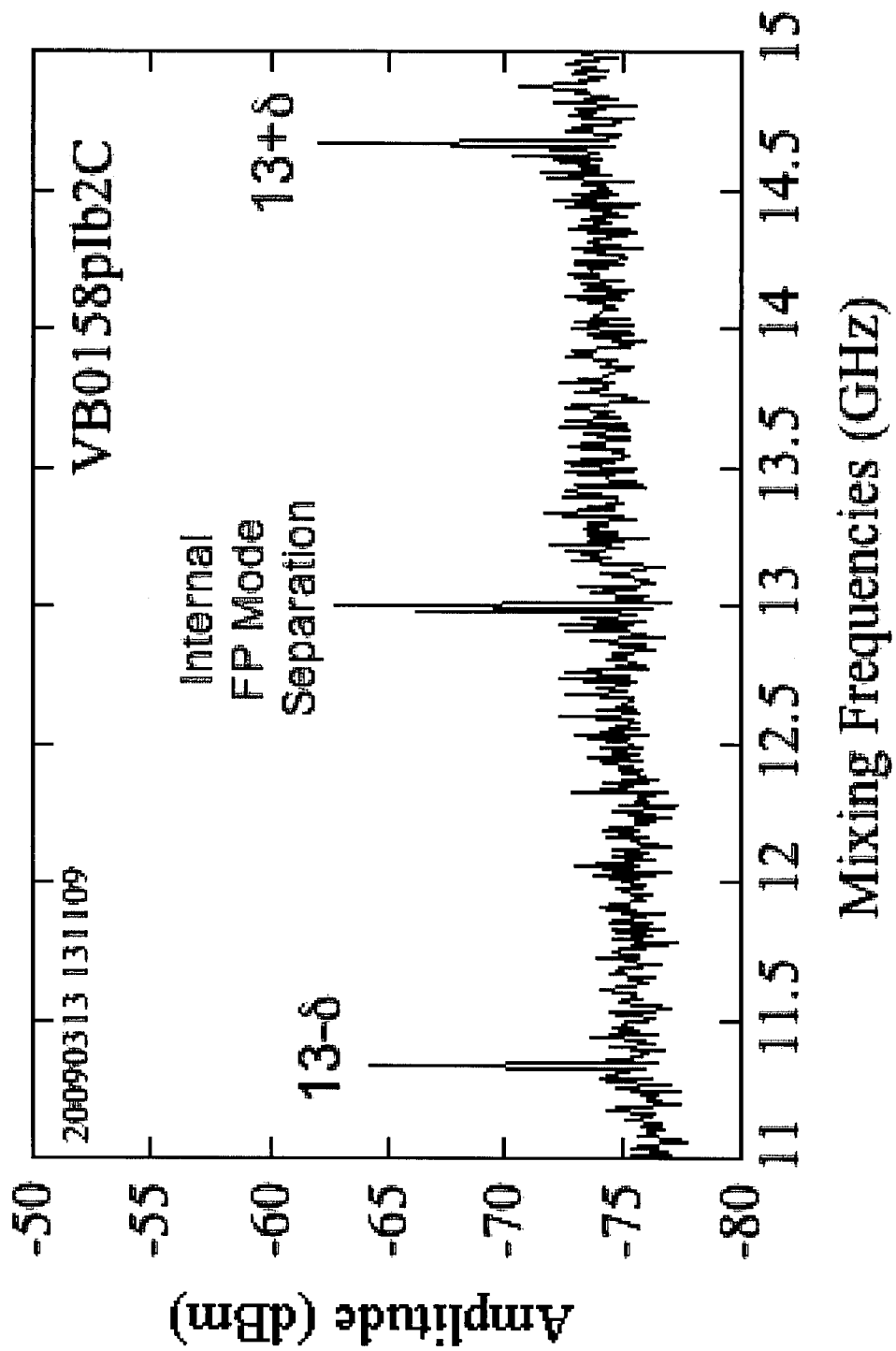
FIGS. 8A-C are plots that show operation of the THz integrated circuit as a heterodyne receiver.
Figure 8B:
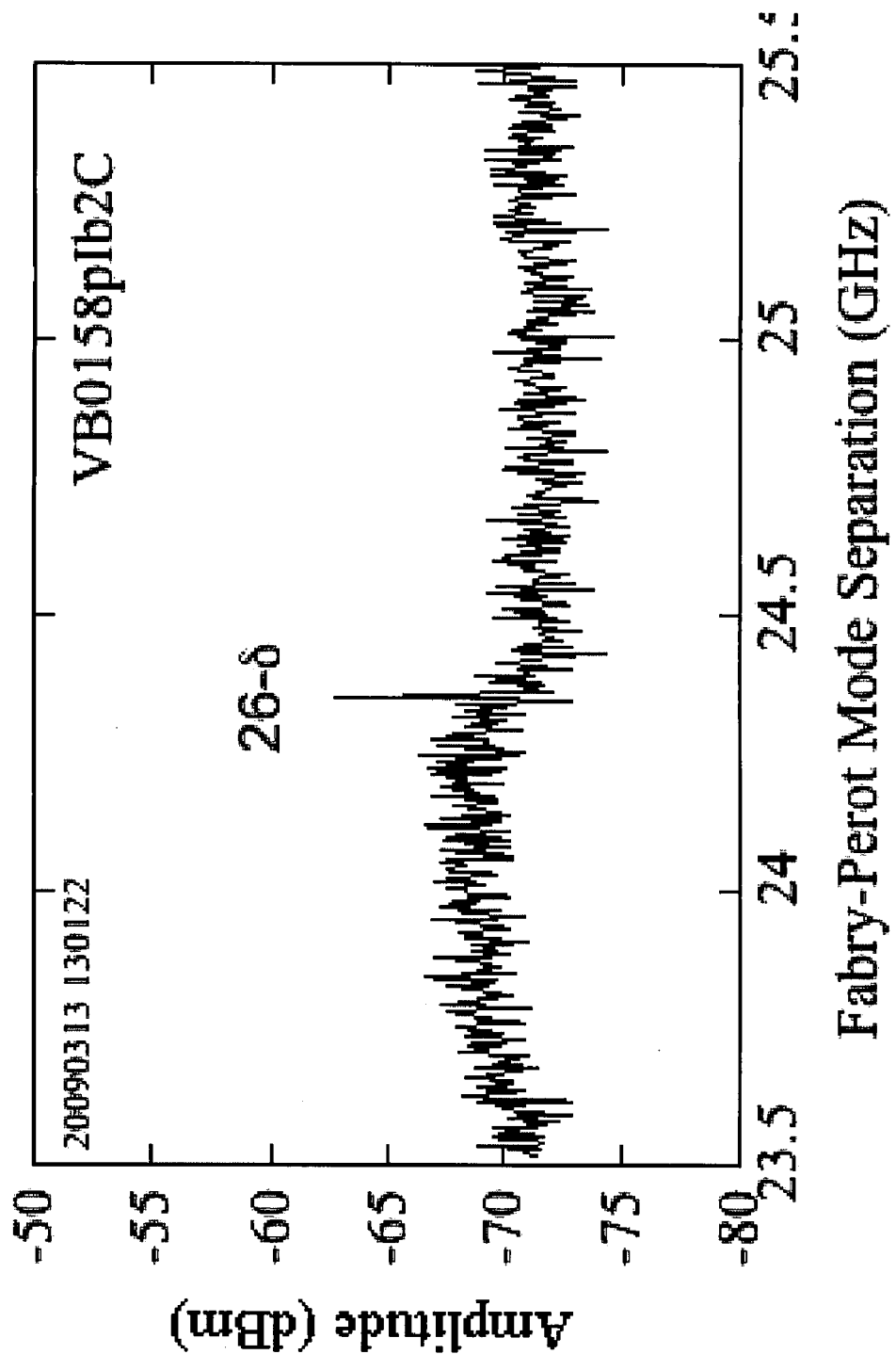
Figure 8C:
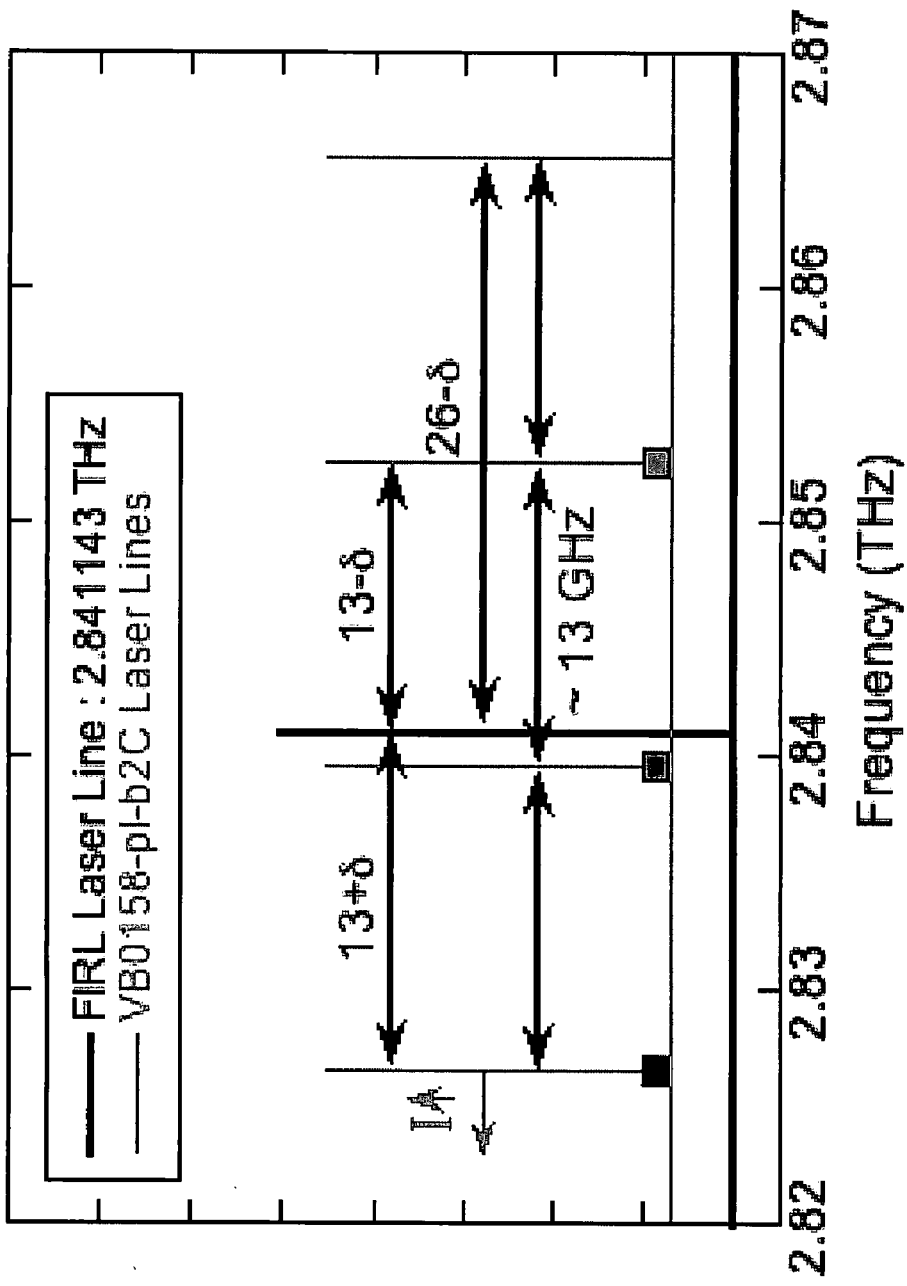

FIGS. 8A-C demonstrate operation of the THz IC as a heterodyne receiver. In the receiver mode, a separate external signal was supplied by a $CO_2$-pumped molecular gas laser, using the 2.841143 THz line of difluoromethane. This molecular gas line was used because it is lies in the middle of the QCL Fabry-Perot modes and therefore is well within 25 GHz of at least one mode of the QCL, putting the received IF signal within the bandwidth of the amplification chain attached to the transceiver's IF output. The external signal was coupled into the integrated transceiver via one edge facet of the QCL ridge waveguide. Heterodyne reception of the molecular gas laser signal was clearly observed via the peaks labeled as 13−δ, 13+δ, and 26−δ in the IF spectra of FIGS. 8A-B. These signal lines are generated as difference frequencies between the molecular gas line and the QCL's F-P mode lines, as shown in FIG. 8C. Here β is the relatively small (~1.7 GHz) frequency difference between the difluoromethane line and the closest mode line of the QCL. The 13−δ and 13+δ signals are then frequency differences between the difluoromethane line and the (respectively) higher and lower adjacent F-P modes, and the 26−δ signal is the difference between the difluoromethane line and the next higher F-P mode.

Sensitivity of this transceiver acting as an integrated heterodyne receiver system was far from optimized, as the minimum detectable RF power was only about 0.1 μW in a 30 kHz bandwidth. Facet coupling of the RF signal is highly inefficient and is estimated to reduce sensitivity by three to four orders-of-magnitude, but an antenna was omitted in this prototype design to simplify fabrication as much as possible. It is also possible that the Schottky diode was underpumped by the QCL LO as the coupling of diode to QCL fields is strongly dependent on the depth of the Schottky interface into the n+ GaAs layer. Such underpumping could significantly degrade the RF-to-IF conversion gain of the diode mixer.

Figure 9:
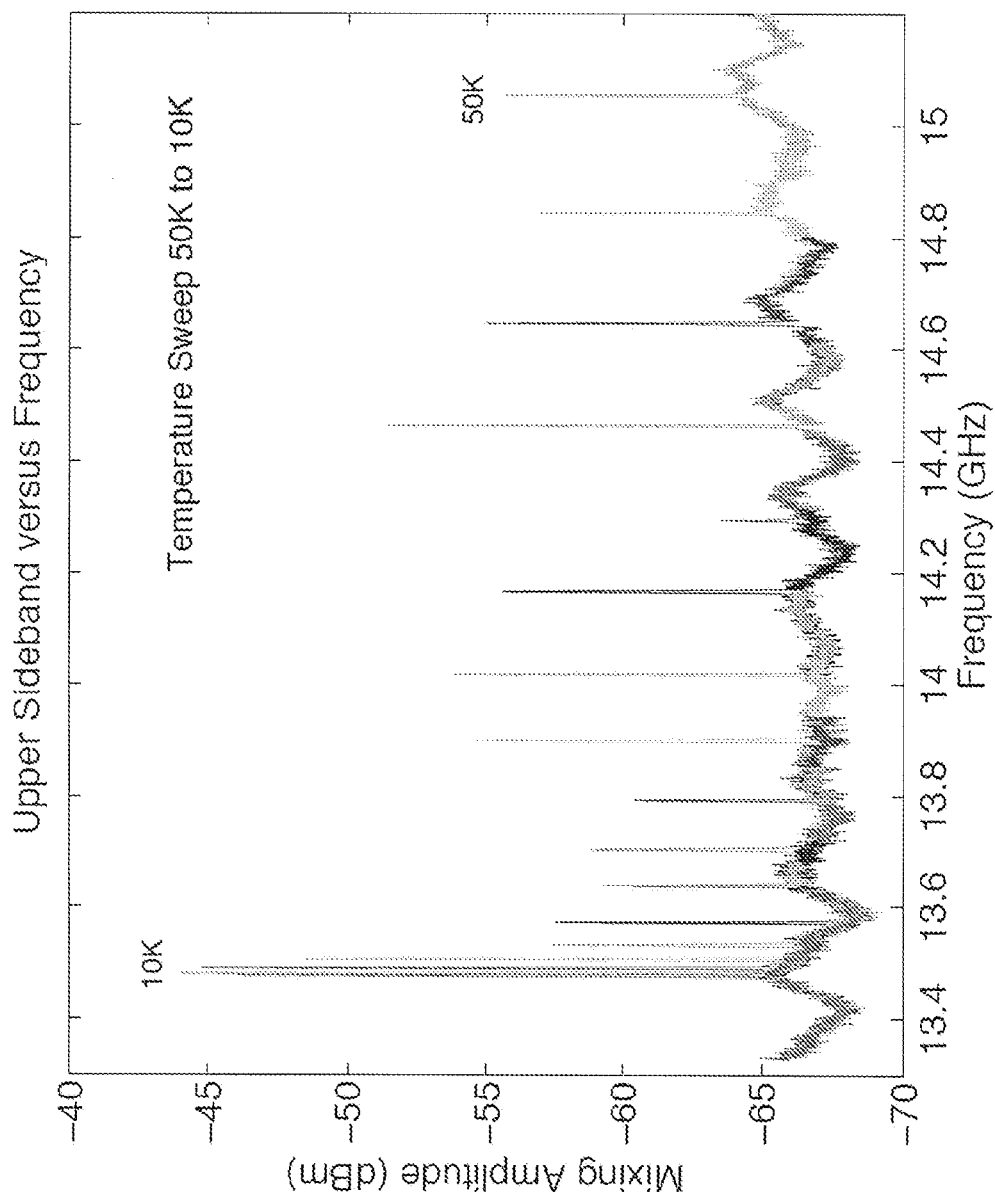
FIG. 9 is a plot that shows the increase in the mixer's IF signal frequency with increasing transceiver operating temperature from 10 K to 50 K.

Besides enabling heterodyne reception in a monolithic THz IC, the integrated diode can also be used to monitor and control the QCL frequency characteristics. FIG. 9 shows the increase in the mixer's IF signal frequency with increasing transceiver operating temperature from 10 K to 50 K. This frequency increase of the IF signal is generated by a gradual increase in the separation between the QCL's F-P modes with increasing temperature. The entire approximately 1.6 GHz range of this mode separation frequency shift is within ¼ of the 0.25 $cm^{-1}$ instrumental line width of high-resolution FTS systems normally used to characterize QCL frequency. Thus, the mode separation's temperature dependence is only barely observable using a FTS, but can be mapped out, using the integrated diode as a probe, at the resolution limited only by the QCL itself (a couple MHz in this case) rather than by instrumental line width.

Figure 10A:
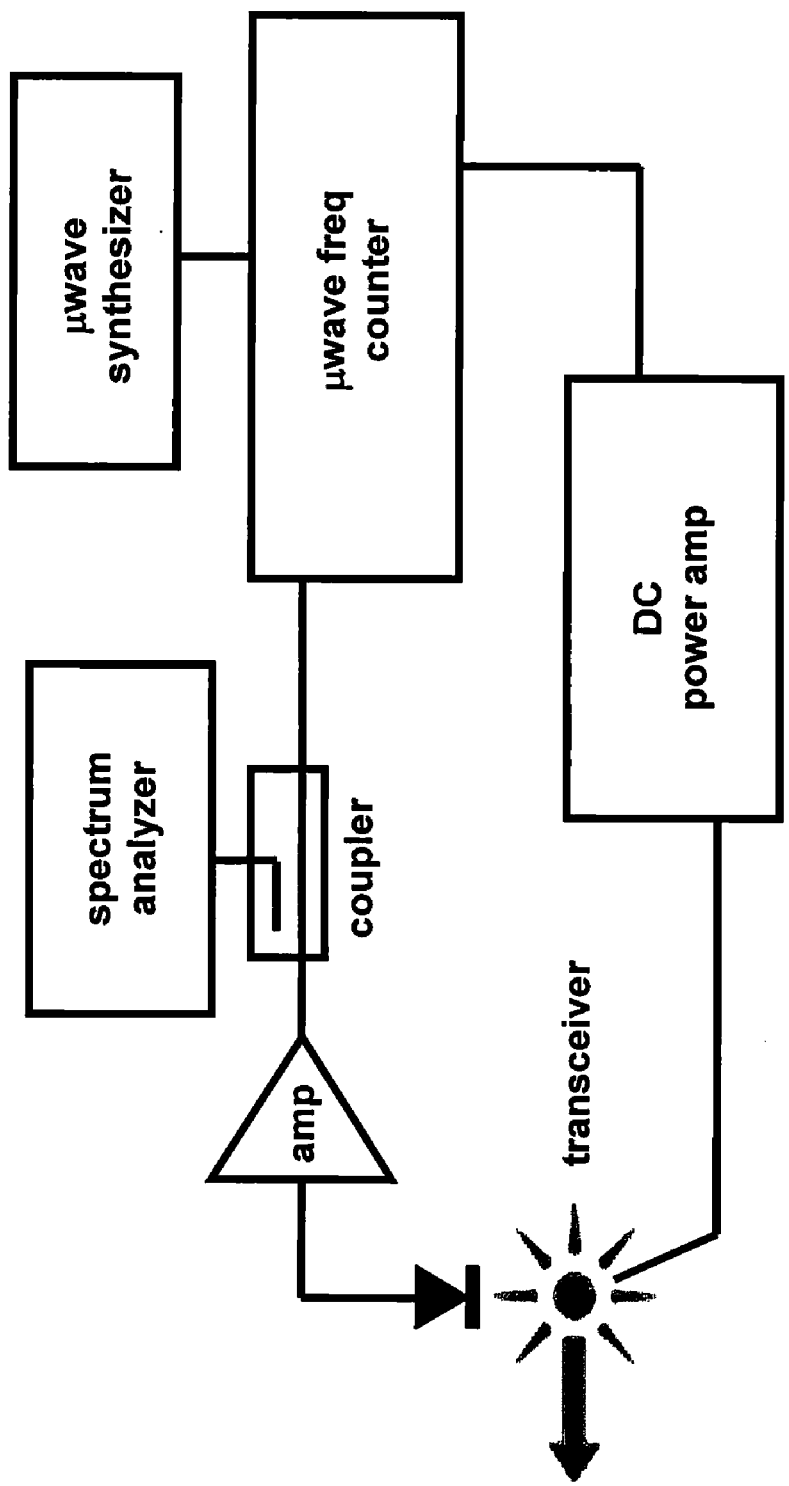
FIGS. 10A-B show how the Fabry-Perot mode difference frequency generated by the diode can be used as an active feedback signal to phase lock the difference modes of the QCL to a microwave reference and hence control the transceiver's output frequency.

The F-P mode difference frequency generated by the diode can also be used as an active feedback signal to phase lock the difference modes of the QCL to a microwave reference and hence control the transceiver's output frequency. In this case, one mode of a multi-mode QCL is considered the LO and one or more of the other internal modes are considered a received THz signal. The IF signal generated by mixing the internal modes can be used to monitor or control the laser. For example, the generated IF signal can be used to lock the differential mode frequency characteristics of the laser. The experimental setup is shown in FIG. 10A. The procedure is similar to that described in Baryshev et al., *Appl. Phys. Lett.*

Figure 10B:
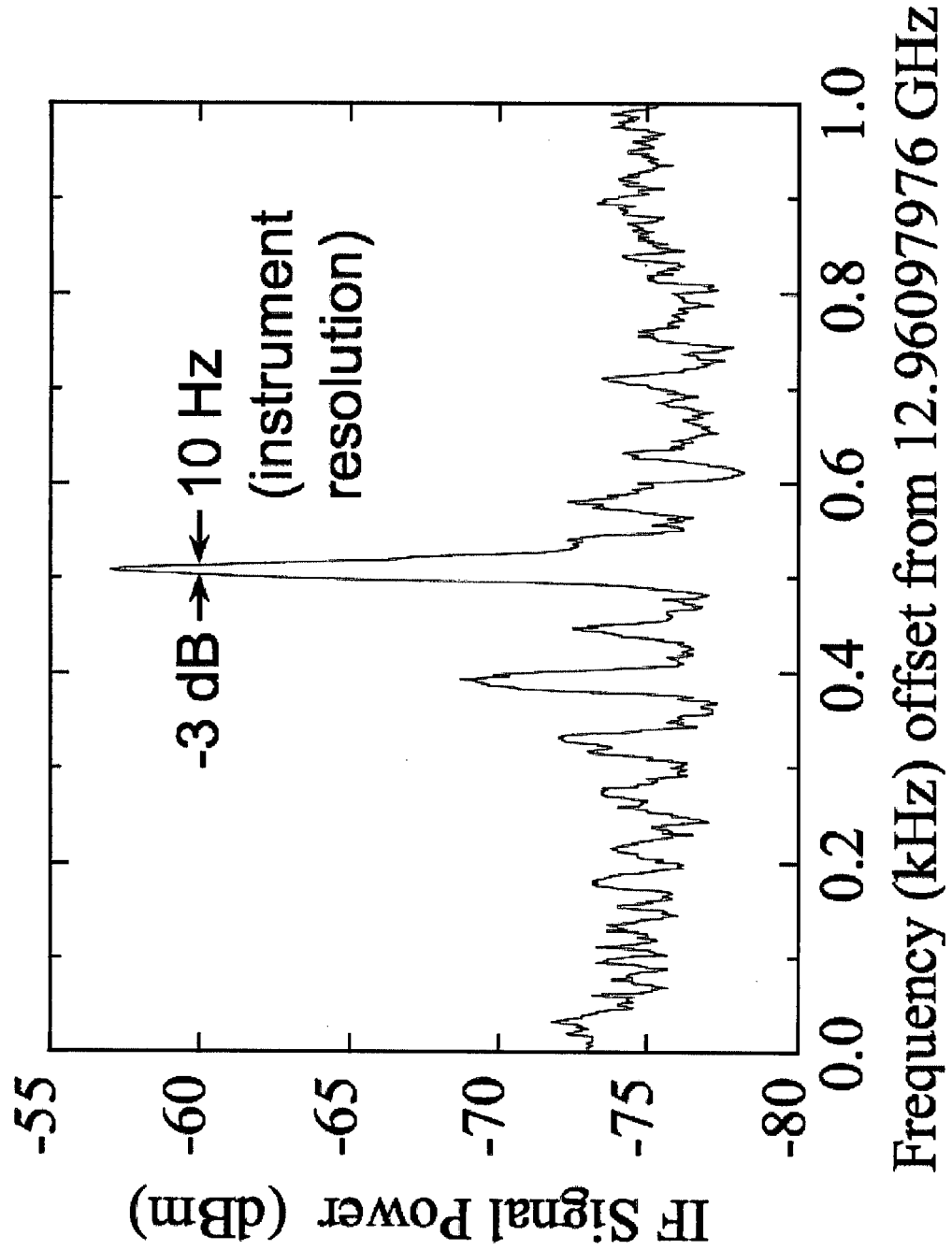

89, 0311165 (2006), where a superconducting hot electron bolometer mixer was used to generate a F-P difference signal from a QCL using quasioptical coupling between separate source and mixer components in different cryostats. The integrated transceiver significantly simplifies the ability to phase lock by eliminating optical coupling between physically separate components. No mirrors, lenses, windows, or mechanical alignment are required, and the transceiver sits in a single cryostat. FIG. 10B shows the IF spectrum of a phase locked integrated transceiver. The linewidth of this IF signal is less than 10 Hz (full width half-maximum), limited by the instrumental resolution bandwidth of the spectrum analyzer. The IF frequency of the locked system was also observed to drift less than 10 Hz over a period of 5 to 10 minutes. Thus the integrated diode can be used to control the differential mode frequency characteristics of the QCL with a very high degree of precision.

The present invention has been described as an integrated heterodyne terahertz transceiver. It will be understood that the above description is merely illustrative of the applications of the principles of the present invention, the scope of which is to be determined by the claims viewed in light of the specification. Other variants and modifications of the invention will be apparent to those of skill in the art.

We claim:

1. An integrated heterodyne terahertz transceiver, comprising:
    a quantum cascade laser, comprising
        a bottom contact layer,
        a layered heterostructure of two or more semiconductor alloys on the bottom contact layer, and
        a top waveguide layer on the layered semiconductor heterostructure, thereby providing an active semiconductor core between the top and bottom layers; and
    at least one Schottky diode, comprising a rectifying metal contact on the top surface of the layered semiconductor heterostructure;
    wherein the quantum cascade laser couples terahertz local oscillator power to the at least one Schottky diode to mix with a received terahertz signal to provide an intermediate frequency output signal.

2. The integrated heterodyne terahertz transceiver of claim 1, wherein the received terahertz signal is received by a horn or antenna on each of the at least one Schottky diodes.

3. The integrated heterodyne terahertz transceiver of claim 2, wherein the antenna comprises a patch or dipole antenna.

4. The integrated heterodyne terahertz transceiver of claim 1, wherein the received terahertz signal is received by an end facet or sidewall of the active semiconductor core, or though the top or bottom layer.

5. The integrated heterodyne terahertz transceiver of claim 1, further comprising an active section that intersects the semiconductor core and wherein the received terahertz signal is received through the active section that amplifies the received terahertz signal.

6. The integrated heterodyne terahertz transceiver of claim 1, wherein the layered semiconductor heterostructure comprises a ridge structure.

7. The integrated heterodyne terahertz transceiver of claim 6, wherein the at least one Schottky diode comprises at least two Schottky diodes that form an array on the ridge structure.

8. The integrated heterodyne terahertz transceiver of claim 1, wherein the two or more semiconductor alloys comprise gallium arsenide.

9. The integrated heterodyne terahertz transceiver of claim 1, wherein the top waveguide layer comprises a metal or a doped semiconductor.

10. The integrated heterodyne terahertz transceiver of claim 1, wherein the bottom contact layer comprises a metal or a doped semiconductor.

11. The integrated heterodyne terahertz transceiver of claim 1, wherein the rectifying metal contact comprises titanium.

12. The integrated heterodyne terahertz transceiver of claim 1, wherein the received terahertz signal has a frequency of 100 GHz to 10 THz.

13. The integrated heterodyne terahertz transceiver of claim 1, further comprising a coplanar waveguide or microstrip line on the layered semiconductor heterostructure to bring off the intermediate frequency output signal.

14. An integrated heterodyne terahertz transceiver, comprising:
    a quantum cascade laser, comprising
        a bottom contact layer,
        a layered heterostructure of two or more semiconductor alloys on the bottom contact layer, and
        a top waveguide layer on the layered semiconductor heterostructure, thereby providing an active semiconductor core between the top and bottom layers; and
    at least one Schottky diode, comprising a rectifying metal contact on the top surface of the layered semiconductor heterostructure;
    wherein the quantum cascade laser couples terahertz local oscillator power to the at least one Schottky diode to measure the power of the laser.

* * * * *